US00RE34936E

United States Patent [19]

Campbell et al.

[11] E Patent Number: Re. 34,936

[45] Reissued Date of Patent: May 9, 1995

[54] ANIMAL MARKER IMPLANTING SYSTEM

[75] Inventors: Neil E. Campbell, Hasbrouck Heights; Chinsoo Park, Rutherford, both of N.J.

[73] Assignee: Bio Medic Data Systems, Inc., Maywood, N.J.

[21] Appl. No.: 96,075

[22] Filed: Jul. 22, 1993

Related U.S. Patent Documents

Reissue of:

[64] Patent No.: 4,787,384
Issued: Nov. 29, 1988
Appl. No.: 919,152
Filed: Oct. 6, 1986

[51] Int. Cl.[6] ..... A01K 11/00

[52] U.S. Cl. ..... 606/117; 606/116; 40/300; 604/62

[58] Field of Search ..... 604/57, 59, 60, 62; 606/116, 117; 40/300

[56] References Cited

U.S. PATENT DOCUMENTS

| | | | |
|---|---|---|---|
| 2,907,327 | 10/1959 | White | 604/60 |
| 3,016,895 | 1/1962 | Sein | 604/60 |
| 3,572,335 | 3/1971 | Robinson | 604/59 |
| 3,620,216 | 11/1971 | Szymanski | 604/60 |
| 3,820,545 | 6/1974 | Jefferts | 128/330 |
| 4,233,964 | 11/1980 | Jefferts et al. | 128/330 |
| 4,262,632 | 4/1981 | Hanton | 119/1 |
| 4,263,910 | 4/1981 | Pardekooper et al. | 604/60 |
| 4,451,253 | 5/1984 | Harman | 604/60 |
| 4,518,384 | 5/1985 | Tarello et al. | 604/62 |
| 4,672,967 | 6/1987 | Smith | 128/330 |
| 4,679,559 | 7/1987 | Jefferts | 128/330 |

FOREIGN PATENT DOCUMENTS

| | | | |
|---|---|---|---|
| 0042719 | 12/1981 | European Pat. Off. . | |
| 0090899 | 10/1983 | European Pat. Off. | 604/62 |
| 2242064 | 3/1975 | France | 604/62 |
| 0806702 | 6/1951 | Germany | 604/60 |
| 0472560 | 9/1937 | United Kingdom . | |
| 1525841 | 9/1978 | United Kingdom . | |
| 2188028 | 9/1987 | United Kingdom . | |

*Primary Examiner*—Stephen C. Pellegrino
*Assistant Examiner*—Glenn K. Dawson
*Attorney, Agent, or Firm*—Stroock & Stroock & Lavan

[57] ABSTRACT

A system for implanting a solid marker in an animal is provided. The apparatus includes a hollow tube having an entrance and an exit opening. A support is provided for supporting a hollow tube. A plunger is slideably disposed between a first position and a second position within the support. The plunger cooperates with the support and the tube. The plunger engages the marker proximate to the entrance opening of the tube, and ejects the marker through the tube when the plunger is moved from a first position to a second position.

16 Claims, 7 Drawing Sheets

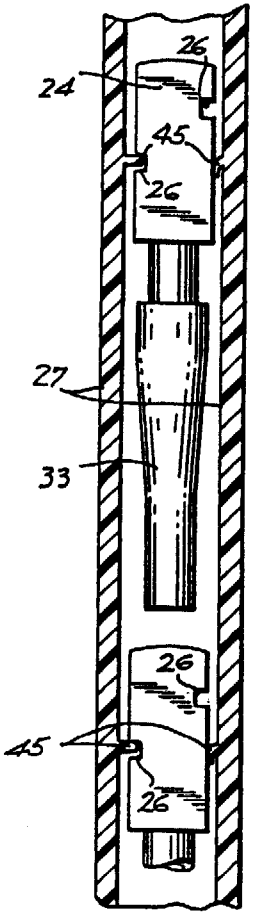
FIG. 5
FIG. 4
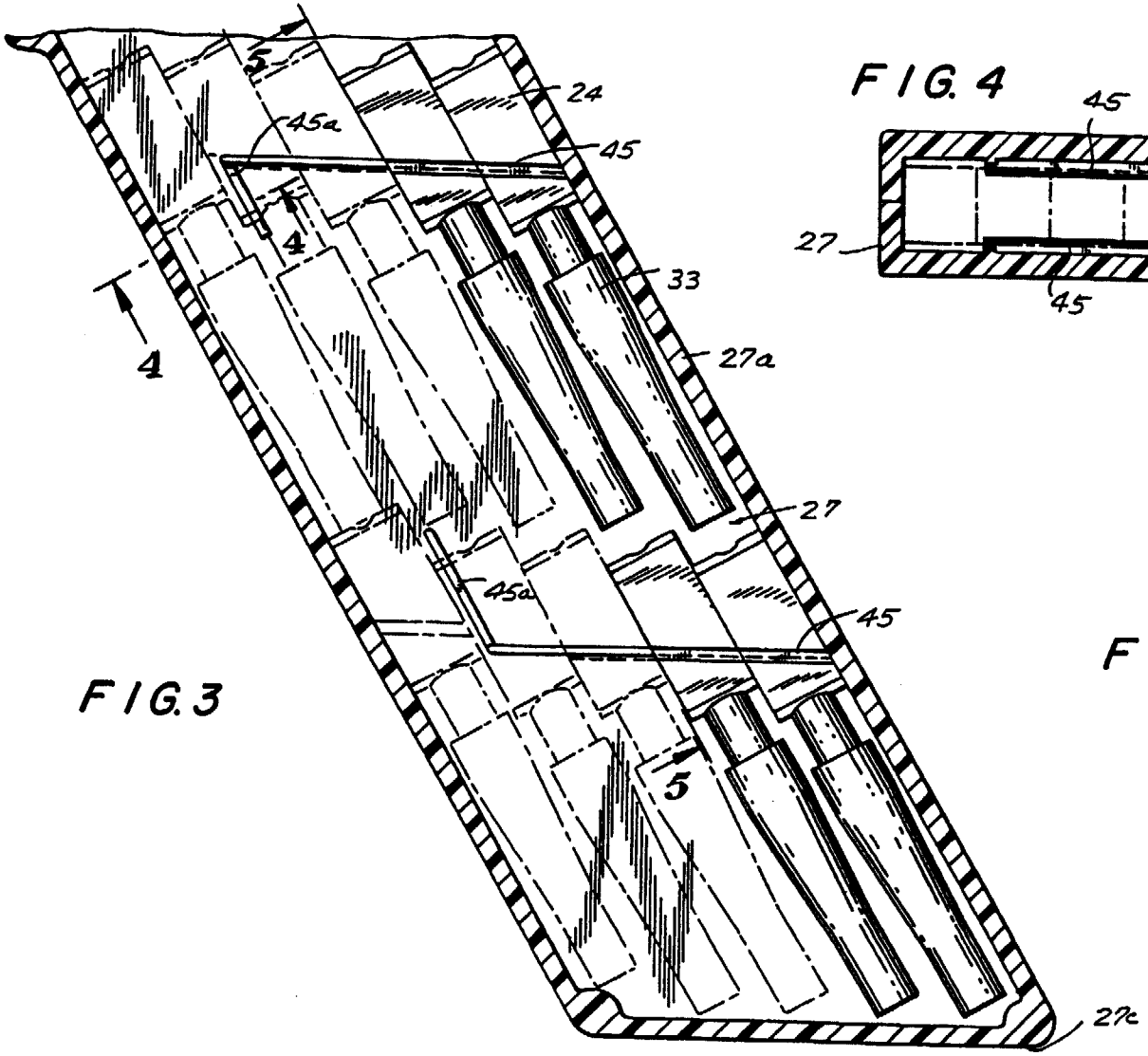
FIG. 3

FIG. 19
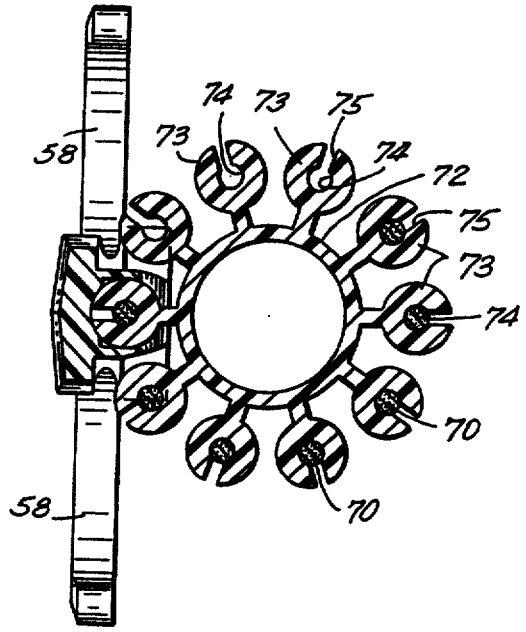
FIG. 20
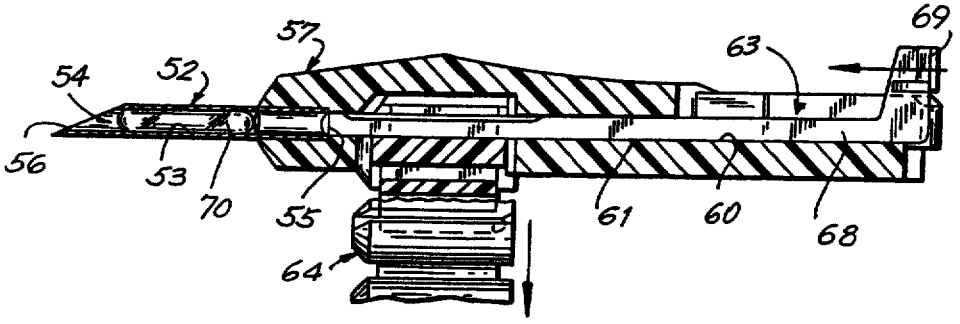
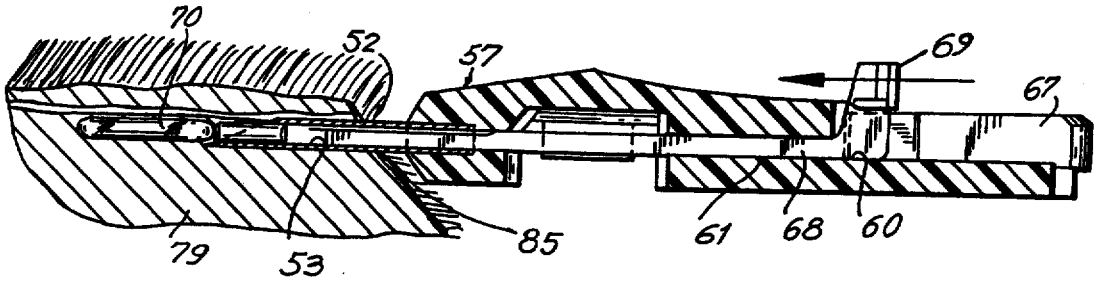
FIG. 21

ANIMAL MARKER IMPLANTING SYSTEM

Matter enclosed in heavy brackets [ ] appears in the original patent but forms no part of this reissue specification; matter printed in italics indicates the additions made by reissue.

BACKGROUND OF THE INVENTION

This invention relates, in general, to a system for implanting an identification marker in an animal and, in particular, to a system for facilitating implantation and retention of an identification marker into a laboratory animal.

Heretofore, the marking of animals for tracking and testing purposes has involved marking the animal externally, i.e., tatooing, branding or tagging. These external markers are difficult to read when identifying the animal and are extremely limited in the mount of information about the animal that can be carried by the external marker.

In order to overcome the disadvantages noted above with external markers, a system has been proposed whereby markers carrying information that can be read by an external detector can be implanted in a test animal. However, such a system requires an instrument that permits a marker to be delivered into the animal without difficulty and wherein the marker will remain securely embedded in the lab animal for a considerable length of time.

SUMMARY OF THE INVENTION

Generally speaking, in accordance with the invention, an improved apparatus for implanting a marker into an animal is provided. The apparatus includes a hollow tube having an opening at each end. An entrance end of the hollow tube is supported within a housing. An exit end of the tube is sharp to allow subcutaneous penetration of the tube underneath the skin of a laboratory animal. A plunger is slideably mounted within the housing. The plunger is adapted to displace the marker from a first position in the tube out of the exit end of the tube.

In an exemplary embodiment, an electronic transponder containing information about the animal, such as identification numbers, is placed in the marker. When the tube is inserted below the skin of the animal and the plunger is displaced, the marker containing the electronic transponder is forced through the tube, lodging it underneath the skin of the animal.

An object of this invention is to provide an improved apparatus for implanting markers in laboratory animals.

A further object of this invention is to provide an implanting system for facilitating identification of laboratory animals.

Still a further object of this invention is to provide an easy to use implanting instrument for implanting a marker into a laboratory animal.

Yet a further object of the invention is to provide an implanting system for implanting a marker subcutaneously in the animal so that the marker will be retained within the animal.

Still other objects and advantages of the invention will in part be obvious and will in part be apparent from the specification and the drawings.

The invention accordingly comprises features of construction, combination of elements and arrangements of parts which will be exemplified in the construction hereinafter set forth and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3 is a partial sectional view taken along line 2—2 of FIG. 1;

FIG. 4 is a partial sectional view taken along line 4—4 of FIG. 3;

FIG. 5 is a partial sectional view taken along line 5—5 of FIG. 3;

FIG. 19 is a sectional view taken along line 19—19 of FIG. 18;

FIG. 20 is a sectional view of the implanting instrument depicted in FIG. 18, in operation; and FIG. 21 is a sectional view of the implanting instrument depicted in FIG. 18, in operation.

DETAILED DESCRIPTION OF THE PREFERRED EMBODIMENTS

Figure 1:
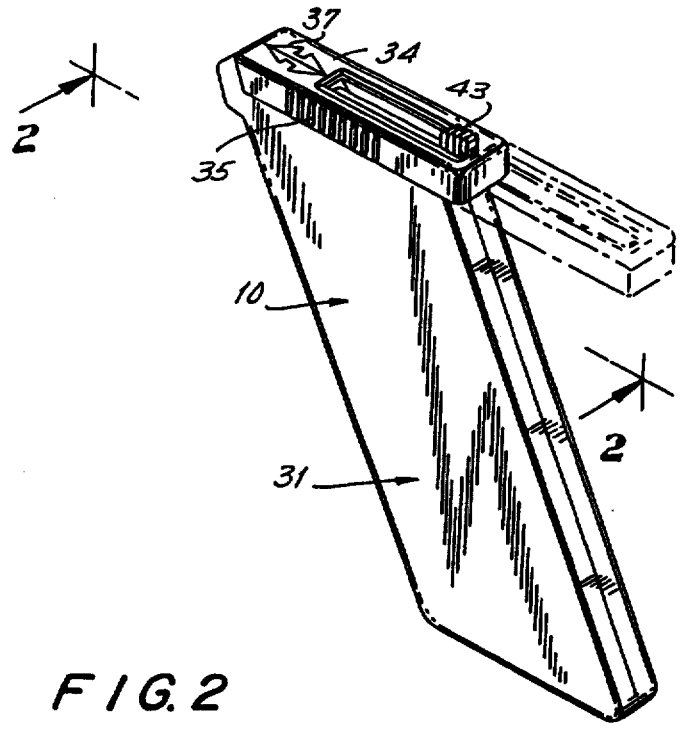
FIG. 1 is a perspective view of an animal marker implanting instrument constructed in accordance with a preferred embodiment of the instant invention.

Reference is initially made to FIGS. 1 through 15, wherein an animal marking system including an implanting instrument, generally indicated at 10 (FIG. 1), a needle assembly, generally indicated as 19 (FIG. 13) and an animal marker, generally indicated as 30 (FIGS. 11, 12 and 14) is depicted. As is explained in greater detail below, the cooperation of the needle assembly, marker and implanting instrument permits the facile implantation of a marker into a laboratory animal and the retention of the marker within the animal during long periods of laboratory monitoring and testing.

Reference is now particularly made to FIGS. 1 through 5, wherein instrument 10 is illustrated in detail.

Instrument 10 defines two opposed half walls 27 which are molded in mirror image and secured together to define a unitary housing in the shape of a handle 31.

Each opposed wall 27 is defined by a substantially parallelogram shaped configuration including lengthwise mating walls 27a and lateral mating walls 27b and 27c. As is explained in greater detail below, mating walls 27a are inclined with respect to lateral mating walls 27b to define handle 31 and to facilitate storage therein of a plurality of needle assemblies. A cap 34 is slideably mounted to the housing defined in opposed wall 27. In an exemplary embodiment, at least one of the opposed walls 27 can be transparent or translucent to allow the user to view the needle assemblies 19 disposed within the handle.

Figure 2:
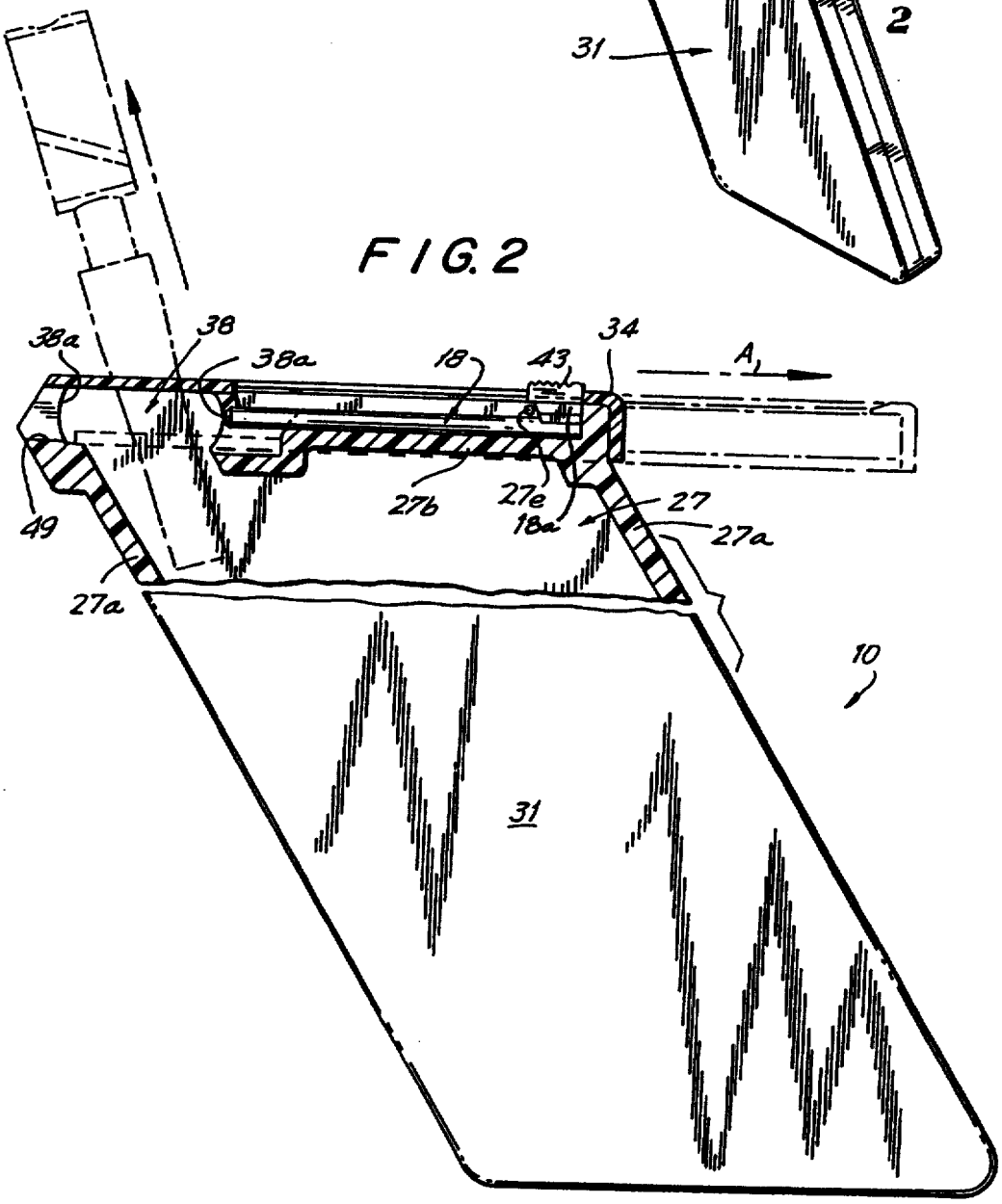
FIG. 2 is a partial sectional view taken along line 2—2 of FIG. 1.
Figures 6, 7, 9, 13:
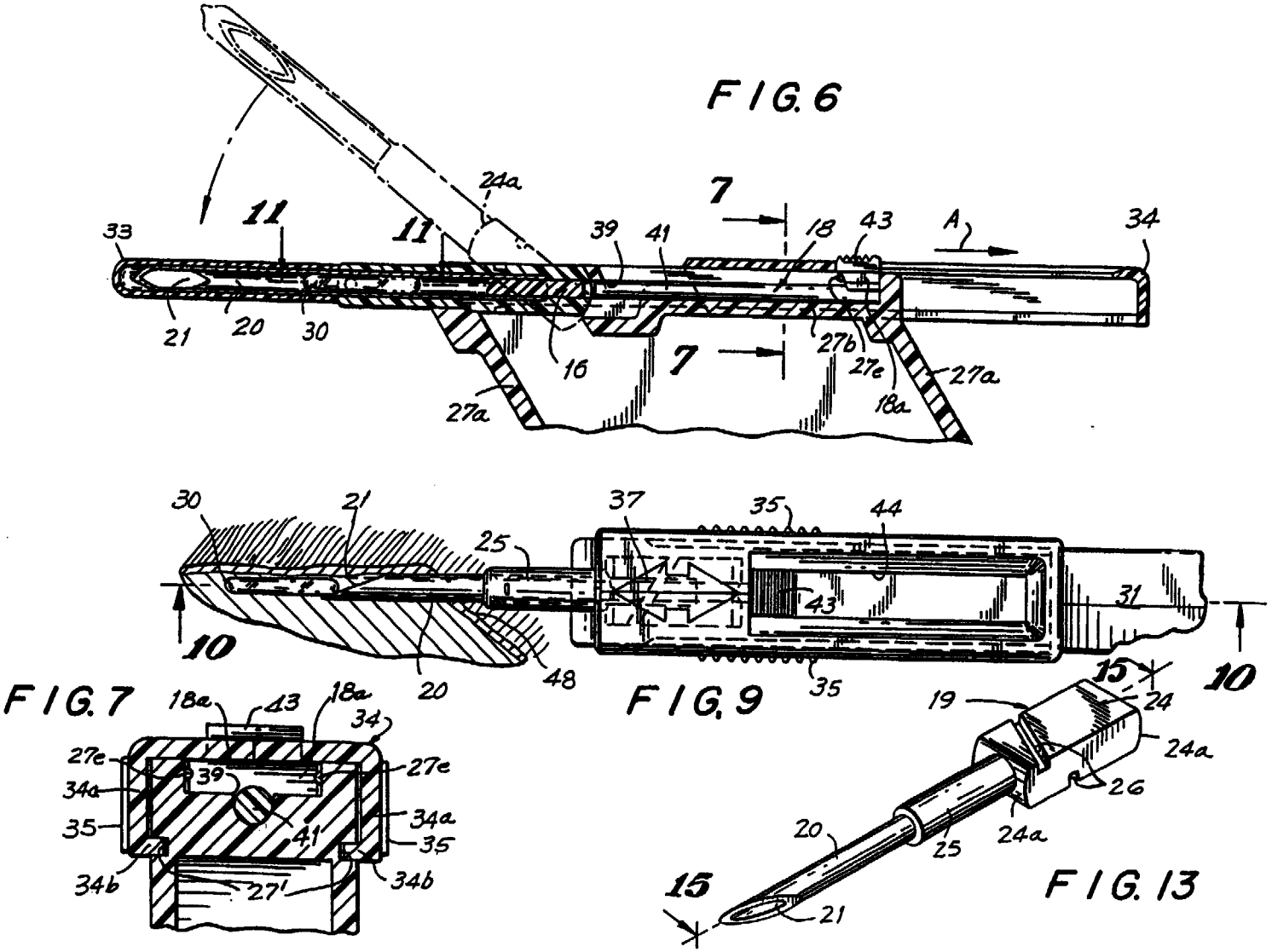
FIG. 6 is a partial sectional view taken along line 2—2 of FIG. 1, when the needle assembly is inserted therein.
FIG. 7 is a sectional view taken along line 7—7 of FIG. 6.
FIG. 9 is a plan view of the implanting instrument illustrated in FIG. 1 in use.
FIG. 13 is a perspective view of the needle assembly.
Figure 10:
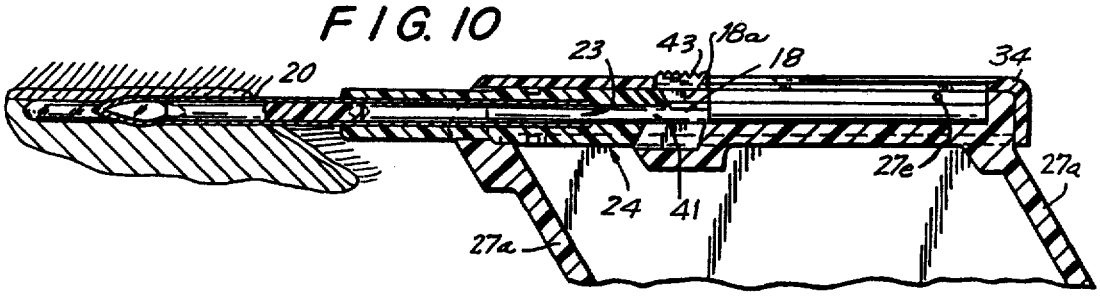
FIG. 10 is a sectional view taken along line 10—10 of FIG. 9.

Cap 34 is normally disposed in a closed position, and can be displaced in the direction A (FIG. 2) from a closed position (solid lines in FIG. 2) to an open position (phantom lines in FIG. 2). As is illustrated in FIG. 7, cap 34 includes side walls 34a and gripping walls 34b which are disposed in elongated slots 27' formed in opposed walls 27. Cap 34 includes ribs 35 on the side for permitting the cap to be easily gripped and can be displaced between an open and closed position. An arrow 37 or other indicia can be imprinted on cap 34 to indicate the proper directions for sliding.

Opposed lateral walls 27b are covered by cap 34 when cap 34 is in a closed position. Opposed lateral walls 27b are configured to define opposed recessed walls 38a and an open chamber, generally indicated at 38, for receiving a needle assembly and for permitting each needle assembly to be dispensed through the opening from the interior of the housing when cap 34 is displaced to an open position. Opposed lateral walls 27b are further configured to define a channel 39 which orients the needle assembly when it is positioned in chamber 38.

Referring particularly to FIGS. 10 through 15, needle assembly 19 is formed from a stainless steel hollow tube 20 having an exit opening 21 and an entrance opening 23. Exit opening 21 is formed in the shape of an inclined edge 22 which forms a sharp point for permitting the tube to easily penetrate an animal's skin. The side of tube 20 having entrance opening 23 is molded in a plug 24. Plug 24 includes a sleeve 25 integrally formed therewith and projecting about tube 20 to extend along a portion of the tube's length. Plug 24 includes arcuate end walls 24a for facilitating the positioning of the plugs in chamber 38 in a manner that will be discussed in detail below. As is particularly illustrated in FIG. 15, marker 30 is positioned in tube 20 near the exit opening 21 thereof. A drive pin 16 is used to position the marker within the tube. Drive pin 16 includes a sealing disc that is integrally molded therewith. Sealing disc 17 has an outside diameter that is sufficient to interference fit with the inside diameter of the tube 20 and prevent displacement of the drive pin during normal stoage and handling of the needle assembly. Drive pin 16 aids in positioning the marker in the tube. However, it has been found necessary to facilitate positioning of the marker in tube 20 particularly when the marker is a glass capsule in order to prevent the marker from slipping out of the exit opening of the tube.

Figure 11:
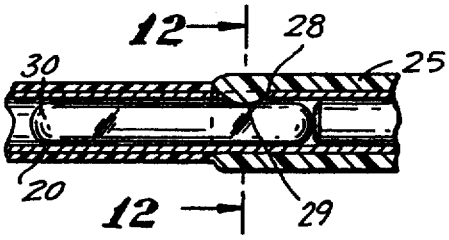
FIG. 11 is an enlarged partial sectional view of the implanter instrument illustrated in FIG. 10.
Figure 12:
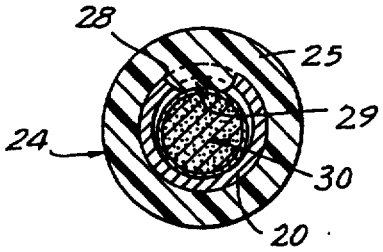
FIG. 12 is a sectional view of the implanting instrument taken along line 12—12 of FIG. 11.

Reference is now made to FIGS. 11 and 12 wherein a projection 29 integral with sleeve 25 extends through opening 28 in order to prevent the marker from slipping or moving in the tube prior to the discharge of same into the animal. This projection can be easily formed during assembly of the hollow tube within plug 24 by molding the plug about the tube and permitting the resin used to form the tube to enter aperture 28. Projection 29 is intended to frictionally engage marker 30 when the marker is positioned within tube 20 to prevent the marker from sliding in the tube. Projection 29 will hold the marker in place until a force sufficient to push marker 30 through tube 20 is applied to a plunger and, in turn, to the marker.

In an exemplary embodiment, tube 20 is stainless steel. However, tube 20 may be made from other rigid FDA approved materials, such as Ultem®, manufactured by General Electric. Also, as aforenoted, sleeve 25 and plug 24 can be integrally formed by injection molding a plastic resin about the entrance opening of tube 20. Also, the sleeve and plug may be formed of rigid materials other than plastic.

Needle assembly 19 is easily positioned in chamber 38 when cap 34 is displaced into an open position. Moreover, needle assembly 19 is tightly secured within chamber 38 by returning cap 34 to a closed position. This prevents any wobbling of the needle 19 assembly during use.

Plunger 18 includes a rod 41 and a knurled surface 43 integrally formed at one end of rod 41. Plunger 18 is slideably mounted within elongated channel 39 formed by lateral walls 27b formed in the top of the housing. Knurled surface 43 projects through elongated opening 44 in cap 34 and permits the plunger to be displaced between a start position and an implanting position. Channel 39 is coaxially aligned with the entrance opening 23 of tube 20 of the needle assembly 19 and alignment channel 49 to form a continuous pathway for rod 41 when needle assembly 19 is retained in chamber 38. Knurled surface 43 extends through elongated opening 44 (FIG. 9) in cap 34, allowing displacement of the plunger 18 by pushing knurled surface 43 from a start position to an implanting position. Plunger 18 also includes seats 18a projecting therefrom which rests against stops 27e formed by opposed half walls 27. Stops 27e and seats 18a cooperate to normally maintain the plunger at the start position depicted in FIG. 6.

The distance of the placement of the marker in the tube from the exit opening and the length of elongated opening 44 have relative lengths with respect to each other. When cap 34 is displaced in the direction A into an open position, it will capture knurled surface 43 if it is not already in a start position and displace the plunger to a start position so that rod 41 is entirely displaced outside of the entrance opening 23 of the needle assembly 19. Furthermore, the distance of the placement of the marker from the exit opening determines the distance through which the rod will be displaced and, hence, the preferred distance of elongaged opening 44. Moreover, this distance further assumes that rod 41 is entirely displaced without the entrance opening of the tube when plunger 18 is in a start position. This permits placement of needle assembly 19 in chamber 38.

When cap 34 is returned to a closed position, stop 27e helps maintain plunger 18 at its start position so that the plunger is not unintentionally pushed forward. If slideable cap 34 is not pushed entirely into a closed position, knurled surface 43 is prevented from being pushed forward sufficiently to cause plunger 18 to eject the marker 28 from the needle assembly 19. This configuration prevents use of the instrument unless the needle assembly 19 is fully secured within chamber 38 and is securely captured by cap 34 being displaced into a closed position. Also, since knurled surface 43 of the plunger 18 comes in contact with the cap at the limits of elongated opening 44, the plunger 18 is automatically positioned by manipulating the cap.

Figure 8:
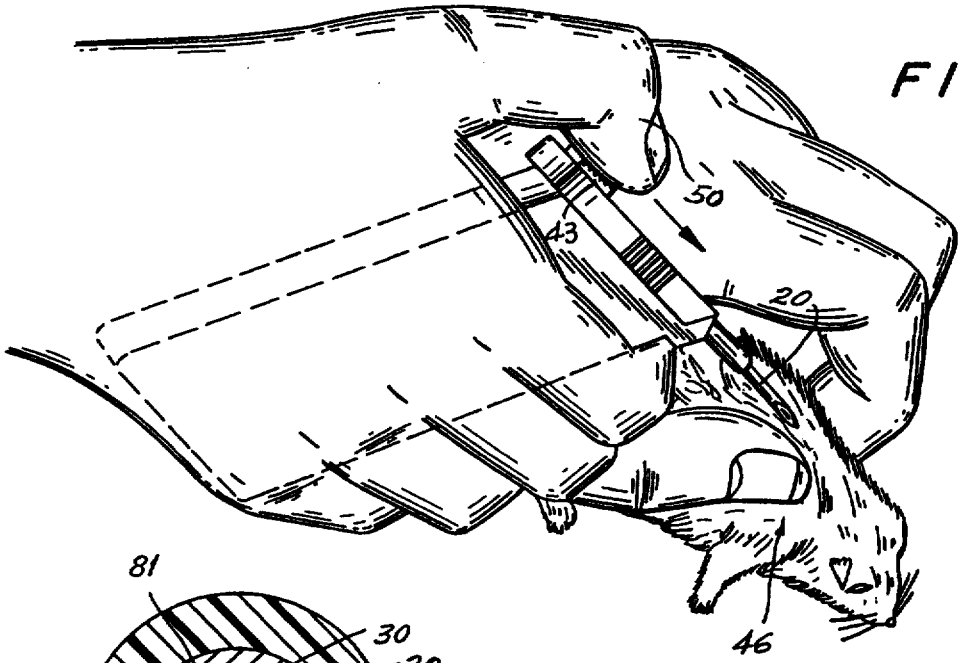
FIG. 8 is a perspective view of the implanting instrument illustrated in FIG. 1 in use.

Reference is now also made to FIG. 8, wherein operation of the instant invention is depicted. In an exemplary embodiment, marker 30 is stored within tube 20 and is retained therein by a projection 25. Cap 34 is then slid into an open position. Needle assembly 19 is then pivotably displaced into chamber 38. Cap 34 is then displaced forward into a closed position supporting and anchoring needle assembly 19 securely in place within chamber 38 and channel 49.

Figure 16:
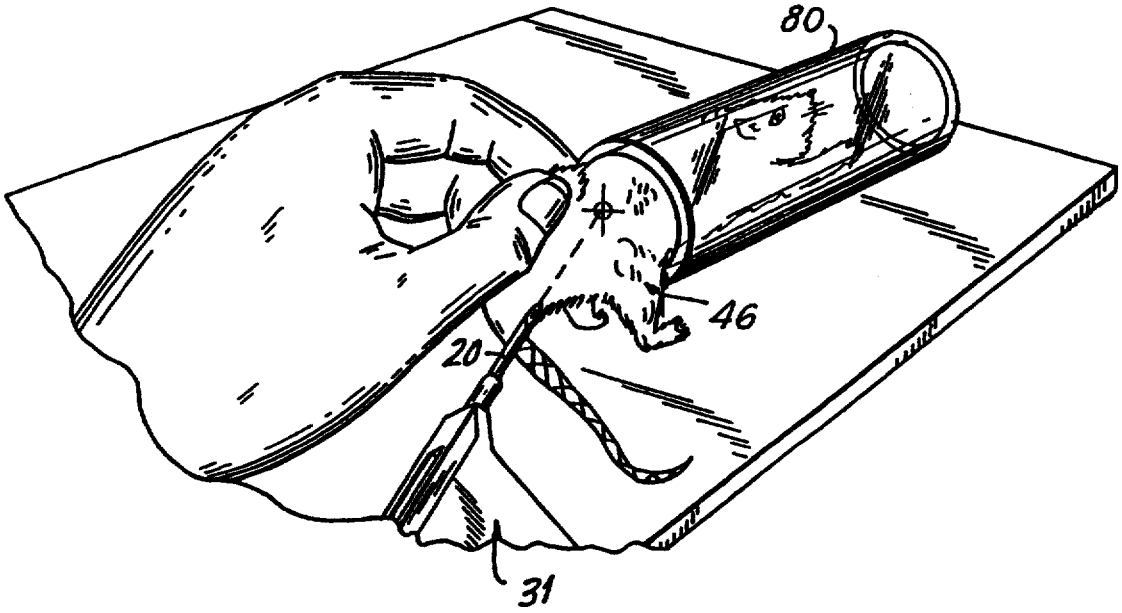
FIG. 16 is a perspective view of a cylinder to be used as part of the instant invention.

Next, a test animal, such as a mouse 46, must be stabilized. As illustrated in FIG. 8, a mouse can be picked up in the user's one hand and the implanting instrument held in the user's other hand. However, as is illustrated in FIG. 16, in an exemplary embodiment, a cylinder 80 that is open at both ends can be utilized to render the head of the mouse immobile. By inserting the mouse's head in a cylinder the mouse cannot turn its head and bite the user's hand or otherwise interfere with the procedure. Furthermore, once the mouse's head is immobilized in the cylinder it permits the hand of the user to be used to stretch the animal's skin and thereby facilitate manipulation of the mouse during subcutaneous implantation. Accordingly, the implanter systems of the instant invention contemplates the use of different sized tubes to accommodate the distinct differences in the size of the laboratory animals. Once the animal is immobilized, the user is prepared to insert tube 20 into the laboratory animal.

Exit end 21 of tube 20 is inserted subcutaneously into mouse 46 until the animal's skin 48 reaches the edge of sleeve 25. This automatically places marker 30 at the desired position beneath the skin. Knurled surface 43 of the plunger 18 is then pushed forward, preferably with the user's thumb 50, with enough force such that plunger 18 engages drive pin 16. Knurled surface 43 is displaced until knurled surface 43 is disposed into an implanting position so that rod 43 comes in contact with the end of opening 44 in cap 34. At this point, plunger rod 41 of plunger 18 has engaged drive pin 16 and extends far enough within tube 20 to have forced drive pin 16 to eject marker 20 from tube 20 underneath the animal's skin. Next, the implanting apparatus is removed from animal skin 48, cap 34 is pulled back and needle assembly 19 is removed and discarded. The process may then be repeated for another animal.

In an exemplary embodiment, marker 30 is a glass capsule having therein an electronic transponder containing identification information about the animal. This is used by way of example only. This process is adaptable to the implantation of any type of marker. Marker 30 is formed by embedding an electronic transponder (not shown) in a glass capsule. By using an electronic transponder, the amount of storable information is greatly increased, especially when transponder information can be directly linked to computer systems containing further information and processing software. Because the capsule is glass, it tends to slide easily in stainless tube 20. It is for this reason that projection 29 is used to interference fit the capsule in the tube and prevent same from moving within the tube during storage and handling of the needle assembly.

Each needle assembly 19 is sealed within a sanitary sleeve 33 which can be easily removed when the needle assembly is displaced into chamber 38 for use in the manner described above. Moreover, after sanitary sleeve 33 is used to cover the exit opening of the tube, a sterilant gas can be injected into a chamber defined by tube 20, drive pin 16 and sealing disc 17 and the sleeve 33. By introducing a sterliant gas, the marker can be sterilized and remain sterilized until the needle assembly is ready for use. Furthermore, as is illustrated particularly in FIGS. 2 through 5 and 13, the opposed side walls 27 of the housing and the plug 24 of each needle assembly are configured in a manner discussed below to permit each needle assembly to be stored in the handle and removed therefrom for easy use.

Specifically, a pair of opposed ramps 45 are formed in each wall 27. Ramps 45 are formed in mirror image on each wall so that they are disposed in registry with each other when walls 27 are brought together to form the housing defining handle 31. Furthermore, each ramp is disposed in parallel with lateral wall 37c and at an angle with respect to the lengthwise extent of the handle. Ramps 45 are spread a sufficient distance apart to permit two rows of needle assemblies to be stored in the handle.

The plug of each needle assembly includes positioning grooves 26 found in opposed surfaces, the grooves being disposed on an angle with respect to the lengthwise extent of the plug and diagonally opposed with each other to facilitate placement of each needle assembly in the housing during assembly of the product. As is illustrated with some particularity in FIGS. 3 through 5, each needle assembly can be positioned within handle by racking the plug onto a first ramp 45 so that the ramp is positioned within the positioning groove 26. The groove 26 and ramp 45 prevent any substantial lengthwise displacement of each needle assembly during storage and use of the instrument. The opposing ramp assists in positioning the plug by pressing against the plug. Each ramp 45 includes a positioning ramp 45a that is parallel with the lengthwise side walls 27a of handle 31. Positioning ramp 45a does not protrude as far as ramp 45 and is provided to assist in preventing the plug from sliding laterally and to further assist in guiding the needle assembly through the opening in chamber 38 when a needle assembly is to be removed from the handle.

In an exemplary embodiment, ten needle assemblies are stored on each ramp 45. As noted above, wall 27a and ramp 45a facilitate delivery of each needle assembly to the operator.

As is illustrated in FIG. 2, the opening in chamber 38 is sufficiently large to permit the needle assembly to be removed therethrough. Accordingly, when a needle assembly is needed, cap 34 is displaced from a closed position to an open position. By manipulating the orientation of the housing, a needle assembly positioned closest to chamber 38 will then slide out of the housing through opening 38. As aforenoted, such manipulation can be facilitated by forming one of the opposed walls 27 forming handle 31 out of a transparent or translucent material. It is then a simple matter to position plug 24 of the needle assembly in chamber 38, slide cap 34 to a closed position and remove the sanitary sleeve 33, so that the user is ready to begin implantation of the marker in the manner discussed above.

Figure 14:
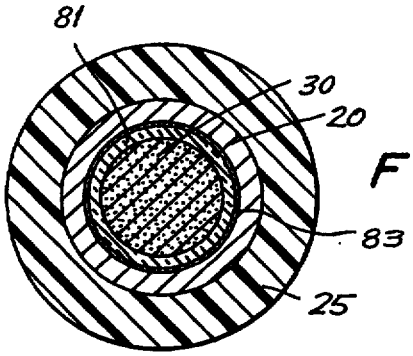
FIG. 14 is a sectional view of the marker depicted in FIG. 11.
Figure 15:
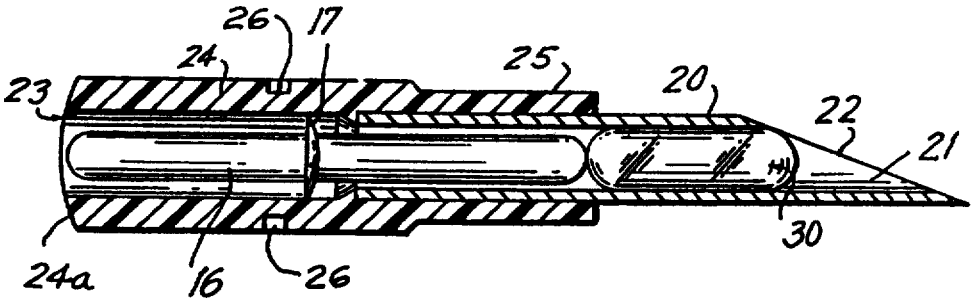
FIG. 15 is a sectional view depicting a sectional view taken along line 15—15 of FIG. 13.

Reference is now made to FIG. 14, wherein a marker 30 is formed of a smooth material 81, such as glass. As aforenoted, the use of a glass marker can be problematical. First, when the needle assembly does not include a projection 29, marker 30 is not secured in the tube and, hence, the marker may slide out of the tube of the needle assembly. Also, it has been observed that when a glass encapsulated transponder is implanted in a laboratory animal, migration of the transponder out of the wound of the animal can occur. Accordingly, in a preferred embodiment, one-half of marker 30 is coated with a layer 83 having a high coefficient of friction. For example, Silastic®, manufactured by Dow Coming, has been successfully used. Also, polypropylene has been used as a coating. By utilizing a layer coating marker 30, projection 29 can be eliminated, thereby allowing for a thinner tube 20 having a greater inner diameter than the embodiments containing projection 29.

The instant invention further contemplates a method of forming layer 38 about a glass marker. Specifically, markers are partially inserted into a mold cavity. Thereafter, a polypropylene resin is injected into the mold cavities and cured about the marker to define a suitable non-slippery surface.

In a further embodiment, the outer surface of glass of marker 30 can be etched. Although etching of the outer glass coating prevents migration in the animal, projection 29 is still needed to hold marker 30 in place in the tube 20. However, etching has been found to weaken the marker and although experimentally viable, does not appear to offer the same efficiency as the use of a coating on the glass capsule.

Figure 17:
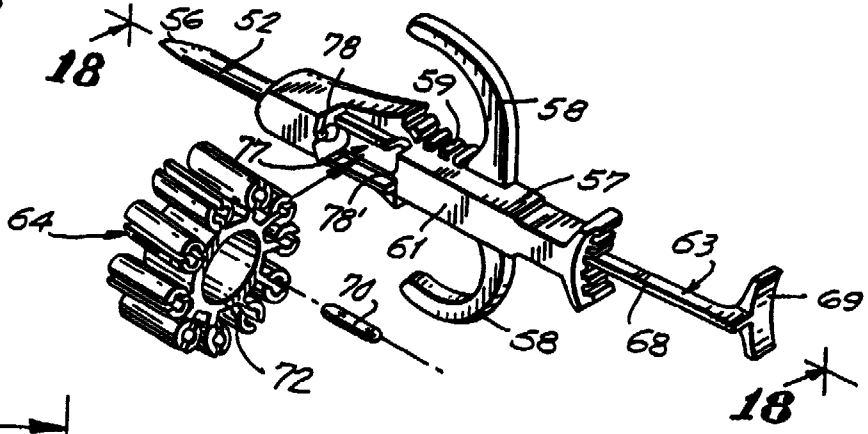
FIG. 17 is an exploded perspective view of an implanting instrument constructed in accordance with an alternative embodiment of the instant invention.
Figure 18:
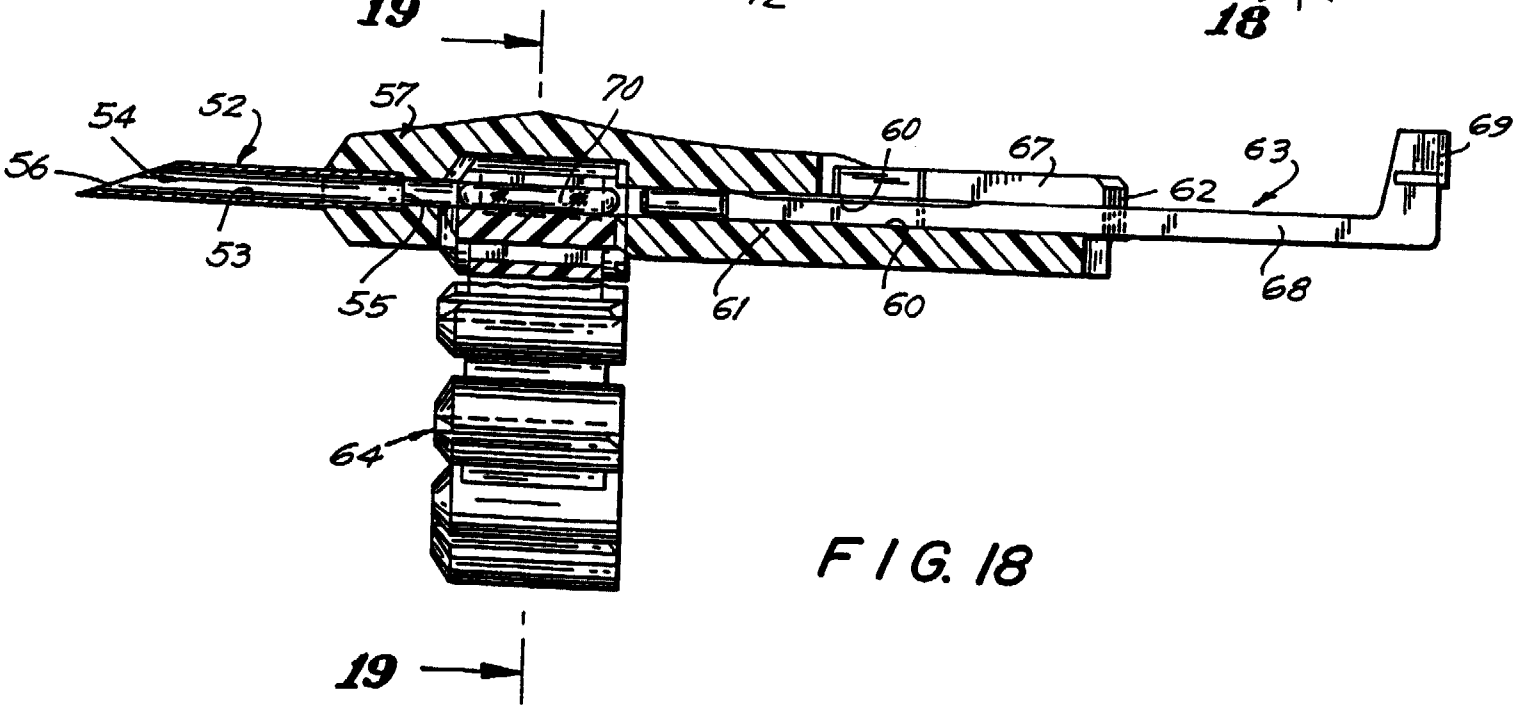
FIG. 18 is a sectional view taken along line 18—18 of FIG. 17.

Reference is now made to FIGS. 17, 18 and 19 wherein an alternate embodiment of the implanting apparatus of the instant invention is depicted. Again, the implanting apparatus includes a needle assembly 52, a housing, generally indicated at 57, and a plunger mechanism, generally indicated as 63.

Housing 57 includes an elongated member 61 having finger retainers 58 integrally projecting therefrom on its opposed sides to prevent rotation of the implanting apparatus during use. Ribs 59 are formed on elongated member 61 opposite retainers 58 to prevent slipping of the fingers, and to give added grip while using the apparatus. A stop 62 is formed at the rear of housing 57 for limiting the displacement of the plunger mechanism.

Needle 52 is fixedly supported within housing 57 and is formed from a hollow tube 53 having an exit opening 54 and an entrance opening 55. Exit opening 54 is characterized by an inclined edge opening 56 which defines a pointed surface. Edge 56 permits easy subcutaneous insertion of the implanting apparatus.

Plunger mechanism 63 includes a rod 68 and a hurled surface 69 integrally formed at one end of rod 68. Plunger mechanism 63 is slideably mounted in an elongated bored opening 60 within housing 57. Elongated bored opening 60 is axially aligned with and forms a continuous pathway with hollow tube Plunger mechanism 63 is slidably disposed in housing 57 and is displaced by pushing on knurled surface 69 in a direction toward exit opening 56 in tube 53. A channel 67 is formed within the top of elongated member 61 and extends from stop 62 to retainers 58. This allows the passage of knurled end 69 past stop 62. When knurled end 69 is displaced forward and comes in contact with the retaining end of the channel, rod 68 extends into needle 52. This causes a marker 70, displaced in the pathway of plunger 63 to be ejected through the exit opening of tube 53.

A marker cartridge assembly, generally indicated as 64, includes a circular hub member 72, and a plurality of marker holders 73 projecting from circular hub member 72. Holders 73 are equally spaced about circular hub member 72. Each holder 73 has a depth that is longer than the length of marker 70. Marker 70 is held within a bore 74 which opens at each end. Bore 74 is sized to interference fit snugly about marker 70 so that a force is needed to push marker 70 loose from bore 74. Each holder 73 of marker cartridge 64 is sized to fit within a chamber 77 formed in elongated member 61. Chamber 77 is axially positioned between tube 53 and elongated opening 60. Chamber 77 is sized to received and retain holder 73 in place within housing 57, and also permits holder 73 to be released when sufficient force is applied to marker cartridge assembly 64. A rib 78 is located on each side of chamber 77 and is positioned in parallel with plunger 63 to assist in securing holder 73 within chamber 77. When in place, bore 74 of holder 73 is axially aligned with plunger 63.

In operation, plunger 63 is displaced to a loading position such that knurled surface 69 is disposed beyond stop 62 and rod 68 is clear of channel 77. The marker cartridge assembly is removed from a sanitary transport package (not shown), and is releasably inserted into chamber 77. Each holder is individually sealed within a sanitary package (not shown) which is torn away when the holder 73 is displaced into chamber 77. As discussed above, in this position plunger mechanism 63, marker 70 contained within holder 73, and needle 52 are all axially aligned. Knurled surface 69 of plunger mechanism 63 is then pushed forward until knurled surface 69 is aligned with stop 62. The length of rod 68 is selected so that it will engage marker 70 in the bore 74 of holder 73 and push marker 70 into the entrance opening 55 of needle 52. Rod 68 is now disposed through bore 74.

Marker cartridge assembly 64 is removed from chamber 77 to keep cartridge assembly 64 from interfering with proper use of the implanting apparatus when injection into the animal occurs. Rod 68 passes through slot 75 allowing easy removal of marker cartridge assembly 64 from cavity 77.

As described above, an animal 79 is then held in either hand, while the implanting apparatus is held in the other hand. Needle 52 is inserted into animal 79 and knurled surface 69 is pushed forward from the stop position to the implanting position so that knurled surface 69 comes into contact with the end of the channel 67 causing rod 68 to be disposed within tube 53 and to eject marker 70 from needle 52 under the animal's skin. The needle 52 is then removed from beneath skin 80, cleaned and another holder 73 having a new marker 70 is inserted into the chamber so that the process can be repeated for a different animal.

It will thus be seen that the objects set forth above, and those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cap all of the generic and specific features of the invention herein described, and all statements of the scope of the invention which, as a matter of language, might be said to fall therebetween.

What is claimed is:

1. An apparatus for implanting a marker in an animal comprising; a hollow tubular means having an entrance opening and an exit opening, a sharp edge formed at the exit opening, support means configured to permit said tubular means to be releasably mounted in said support means, said support means includes a housing and a chamber in said housing, said chamber being adapted to receive said tubular means, and a cover slideably mounted to said housing and adapted to be disposed between a first position in which said tubular means can be inserted into said chamber and a second position wherein said tubular means is maintained securely within said chamber and projects from said housing; and a plunger means, slidably disposed between a first position and a second position, said plunger means operatively supported by said housing and adapted to enter said tubular means when said tubular means is maintained securely in said housing and is displaced from a first position to a second position and to engage said marker of said tubular means for ejecting said marker through said exit opening in response to said plunger means being coordinately displaced from said first position to said second position.

2. An apparatus for implanting a marker as claimed in claim 1, wherein said housing is configured to store said tubular means therein, said chamber including an opening for permitting each said tubular means stored in said housing to be dispensed therethrough.

3. An apparatus for implanting a marker as claimed in claim 2, wherein the housing comprises at least a pair of opposed ramp means projecting from said housing, each said tubular means containing a pair of diagonally opposed slots therein, said slots being dimensioned to operate with said ramps to position each said tubular means in place in said housing and permit said tubular means to slide along one of said ramps.

4. An apparatus for implanting a marker as claimed in claim 1, wherein said plunger means includes a rod and a knurled surface integrally formed at one end of said rod, said knurled surface projecting through said cover to permit said plunger means to be displaced.

5. An apparatus for implanting a marker as claimed in claim 4, wherein said cover has an elongated opening and said knurled surface extends through said elongated opening in said cover to allow displacement of said knurled surface within said opening.

6. An apparatus for implanting a marker as claimed in claim 5, wherein the rod is of a first predetermined length and said opening in said cover is a second predetermined length so that said cover displaces said knurled surface and rod to a position without said chamber when said cover is displaced into an open position so that said tubular means can be releasably inserted in said chamber.

7. An apparatus for implanting a marker as claimed in claim 1, wherein said tubular means including a friction means projecting therein for frictionally engaging a marker within said tubular means and preventing said marker from movement therein during storage and handling of the tubular means.

8. An apparatus for implanting a marker as claimed in claim 7, wherein said means for retaining the marker in place comprises an opening in a side of said tubular means, a projection extending through said opening and projecting in contact with said marker with sufficient force to secure said marker within said tubular means during storage and handling thereof.

9. An apparatus for implanting a marker as claimed in claim 8, wherein said marker is contained within said tubular means proximate to said exit opening.

10. An apparatus for implanting a marker as claimed in claim 1, wherein a layer of material surrounds at least a portion of said marker and provides a friction surface for preventing movement of said marker in said tubular means during storage and handling of said tubular means.

11. A needle assembly for use in an implanting apparatus including a hollow tube having an exit opening and an entrance opening, a marker positioned in said tube proximate to said [entrance] *exit* opening wherein said marker includes a coating thereon for defining an interference fit of said marker in said tube and a drive pin means disposed in said tube between said marker and said entrance opening for positioning said tube, said marker being a glass capsule and said coating being of a non-glass material.

12. A needle assembly as claimed in claim 11, and including a plug means formed about said tube at the entrance opening thereof to permit insertion of the tube into a suitable implantation implement.

13. A system for implanting a marker in a laboratory animal comprising an apparatus for implanting a marker in an animal including a hollow tubular means having an entrance opening and an exit opening, configured to permit said tubular means to be releasably mounted in said support means wherein said support means includes a housing and a chamber in said housing, said chamber being adapted to receive said tubular means, and a cover slideably mounted to said housing and adapted to be disposed between a first position in which said tubular means can be inserted into said chamber and a second position wherein said tubular means is maintained securely within said chamber and projects from said housing and a plunger means, slideably disposed between a first position and a second position, said plunger means cooperatively supported by said housing and adapted to enter said tubular means when said tubular means is maintained securely in said housing and is displaced from a first position to a second position and to engage said marker in said tubular means for ejecting said marker through said exit opening in response to said plunger means being coordinately displaced from said first position to said second position, and that can be grasped in an operator's hand, and an open cylinder adapted to receive and immobilize the head of an animal so that said instrument can be operated without difficulty.

14. An apparatus for implanting a marker in an animal comprising; a hollow tubular means having an entrance opening and an exit opening, a housing configured to permit said tubular means to be releasably held in said housing and a plunger means, slideably disposed between a first position and a second position, said plunger means cooperatively supported by said housing and adapted to enter said tubular means when displaced from a first position to a second position and to engage said marker in said entrance opening of said tubular means for ejecting said marker through said exit opening in response to said plunger means being coordinately displaced from said first position to said second position, and wherein said housing is configured to store said tubular means therein, said housing including an opening for permitting each said tubular means stored in said housing to be dispensed therethrough, wherein said housing means comprises at least a pair of opposed ramp means projecting from said housing, each said tubular means containing a pair of diagonally opposed grooves formed therein, said grooves being dimensioned to receive said ramps and position each of said tubular means in said housing and permit said tubular means to be dispensed through said opening one at a time.

15. The apparatus for implanting a marker of claim 14, further including a second pair of opposed ramp means projecting from said housing, said second pair of opposed ramp means being disposed within said housing below said first ramp means to position a second plurality of said tubular means within said housing and permit said tubular means to be dispensed through said opening one at a time after completion of the dispensing of said tubular means positioned on said first ramp means.

16. The implanting apparatus of claim 14, further including positioning means located at an end of the opposed ramp means positioned closest to said opening of said housing to prevent lateral sliding of said tubular means and guide said tubular means through the opening in the housing.

* * * * *